United States Patent
Hsu et al.

(10) Patent No.: US 11,210,146 B1
(45) Date of Patent: Dec. 28, 2021

(54) INTEGRATION OF MEDICAL DATA SYSTEMS USING EMULATION OF USER INTERFACE

(71) Applicant: Curogram, Inc., Los Angeles, CA (US)

(72) Inventors: Michael Chia-Kei Hsu, Irvine, CA (US); Shayan Jamshid Nafisi, Los Angeles, CA (US)

(73) Assignee: Curogram, Inc., Los Angeles, CA (US)

( * ) Notice: Subject to any disclaimer, the term of this patent is extended or adjusted under 35 U.S.C. 154(b) by 0 days.

(21) Appl. No.: 16/891,746

(22) Filed: Jun. 3, 2020

Related U.S. Application Data

(60) Provisional application No. 62/858,332, filed on Jun. 7, 2019.

(51) Int. Cl.
| | |
|---|---|
| *G06F 9/54* | (2006.01) |
| *G06F 21/31* | (2013.01) |
| *G16H 40/67* | (2018.01) |
| *G06F 8/71* | (2018.01) |
| *G06F 16/25* | (2019.01) |
| *G16H 10/60* | (2018.01) |

(52) U.S. Cl.
CPC ............... *G06F 9/541* (2013.01); *G06F 8/71* (2013.01); *G06F 16/258* (2019.01); *G06F 21/31* (2013.01); *G16H 40/67* (2018.01); *G16H 10/60* (2018.01)

(58) Field of Classification Search
None
See application file for complete search history.

(56) References Cited

U.S. PATENT DOCUMENTS

| | | | | |
|---|---|---|---|---|
| 2009/0287500 | A1* | 11/2009 | Benjamin | G16H 40/67 705/2 |
| 2013/0246932 | A1* | 9/2013 | Zaveri | G06F 3/04815 715/740 |
| 2013/0346109 | A1* | 12/2013 | Gunn | G16H 10/60 705/3 |
| 2018/0091511 | A1* | 3/2018 | Vendrell | H04L 63/10 |
| 2018/0330060 | A1* | 11/2018 | Biles | G16H 50/30 |

* cited by examiner

*Primary Examiner* — Charles E Anya
(74) *Attorney, Agent, or Firm* — Fenwick & West LLP

(57) ABSTRACT

Embodiments relate to the integration of a third-party application with a primary software platform and the integration of multiple different software platforms through user emulators that emulate user input operations. The user emulator enables interoperability between one or more software platforms by using the user emulator to communicate with primary software platforms while using application programming interfaces to interface with third-party applications. In an embodiment, first and second disparate software platforms are accessed. First sessions are initiated with the first and second software platform. First user input operations are emulated on the first software platform to receive a first page of information. A first format of the first page of information is converted to a second formed to write the converted page of information to the second software platform. The user emulator may write additional pages of information to the second software platform from additional software platforms.

20 Claims, 9 Drawing Sheets

600

---

Access a first healthcare software platform and a second healthcare software platform
605

↓

Initiate first sessions with the first healthcare software platform and the second healthcare software platform
610

↓

Emulate first user input operations on the first healthcare software platform to receive a first page of information
615

↓

Convert a first format of the first page of information to a second format to write the converted first page of information to the second healthcare software platform
620

FIG. 6

INTEGRATION OF MEDICAL DATA SYSTEMS USING EMULATION OF USER INTERFACE

CROSS-REFERENCE TO RELATED APPLICATION

This application claims priority under 35 U.S.C. § 119(e) to U.S. Provisional Patent Application No. 62/858,332, filed on Jun. 7, 2019, which is incorporated by reference herein in its entirety.

BACKGROUND

This disclosure generally relates to integrating software platforms, and specifically to integrating software platforms by emulating user input operations.

In current systems, integration of third-party software with a primary software platform can be challenging and time consuming. This is often because many primary software platforms do not offer APIs or utilize protocols that coordinate interaction between the primary software platform and third-party software platforms. For example, many software platforms designed for operating medical practices and storing patient information, such as practice management systems (PMs) or electronic medical record systems (EMRs), do not offer public APIs for integration, or they utilize an industry standard protocol such as HL7 that requires significant coordination between the third-party software and the primary software platform. As a result, to implement connectivity between third-party software and a primary software platform, a large amount of time and extensive collaboration between the developers of the third-party applications and the primary software is often required, making connectivity impractical and cost prohibitive.

Similarly, integration of two primary software platforms can be difficult, especially when one software platform does not offer a public API or utilizes a protocol that requires significant coordination between the two primary software platforms. For example, many software platforms designed for operating medical practices and storing patient information (PMs and EMRs) do not offer a way to communicate or exchange data between the two primary software platforms. This makes it difficult for users of different PMs and EMRs to collaborate.

SUMMARY

Embodiments relate to integration of a third-party application with a primary software platform or the integration of two or more different primary software platforms through one or more user emulators that emulate user input operations. The user emulator may enable interoperability between one or more primary software platforms and the third-party application by using the user emulator to communicate with the primary software platforms while using an application programming interface (API) to interface with the third-party application. By dedicating a user emulator to each primary software platform and using multiple user emulators, a Hub and Spoke model can be embodied where the user emulators function as the Hub and the primary software platforms function as Spokes.

In an embodiment, first and second disparate healthcare software platforms are accessed. The first healthcare software platform may be a primary software platform and/or a third-party software. Similarly, the second healthcare software platform may be a primary software platform and/or a third-party software. The first healthcare software platform and/or second healthcare software platform may be accessed through an API of a user emulator, an API of the first healthcare software platform, an API of the second healthcare software platform, and the like. First sessions are initiated with the first healthcare software platform and the second healthcare software platform. For example, sessions may be initiated by performing authentication of a user by sending authentication information of the user to the first healthcare software platform and/or the second healthcare software platform. First user input operations are emulated on the first healthcare software platform to receive a first page of information. Emulating first user input operations may include triggering one or more API calls of an API of the first healthcare software platform. A first format of the first page of information is converted to a second format to write the converted page of information to the second healthcare software platform. In addition, the first page of information may be parsed to determine a version and a type of the first healthcare software platform before converting the format of the first page of information.

The user emulator may write additional pages of information to the second healthcare software platform from the first healthcare software platform and/or additional healthcare software platforms, such as additional primary software platforms and/or third-party software. For example, the user emulator may access a third healthcare software platform, and initiate second sessions with the second healthcare software platform and the third healthcare software platform. The user emulator emulates second user input operations on the third healthcare software platform to receive a second page of information. To emulate second user input operations, the user emulator may trigger one or more API calls of an API of the second healthcare software platform, an API of the third healthcare software platform, an API of the user emulator, or an alternative and distinct API. The user emulator converts a third format of the page of information to the second format to write the converted second page of information to the second healthcare software platform.

BRIEF DESCRIPTION OF THE DRAWINGS

FIG. 6 is a flow chart of a method for interfacing healthcare software platforms, according to one embodiment.

Figure 1:
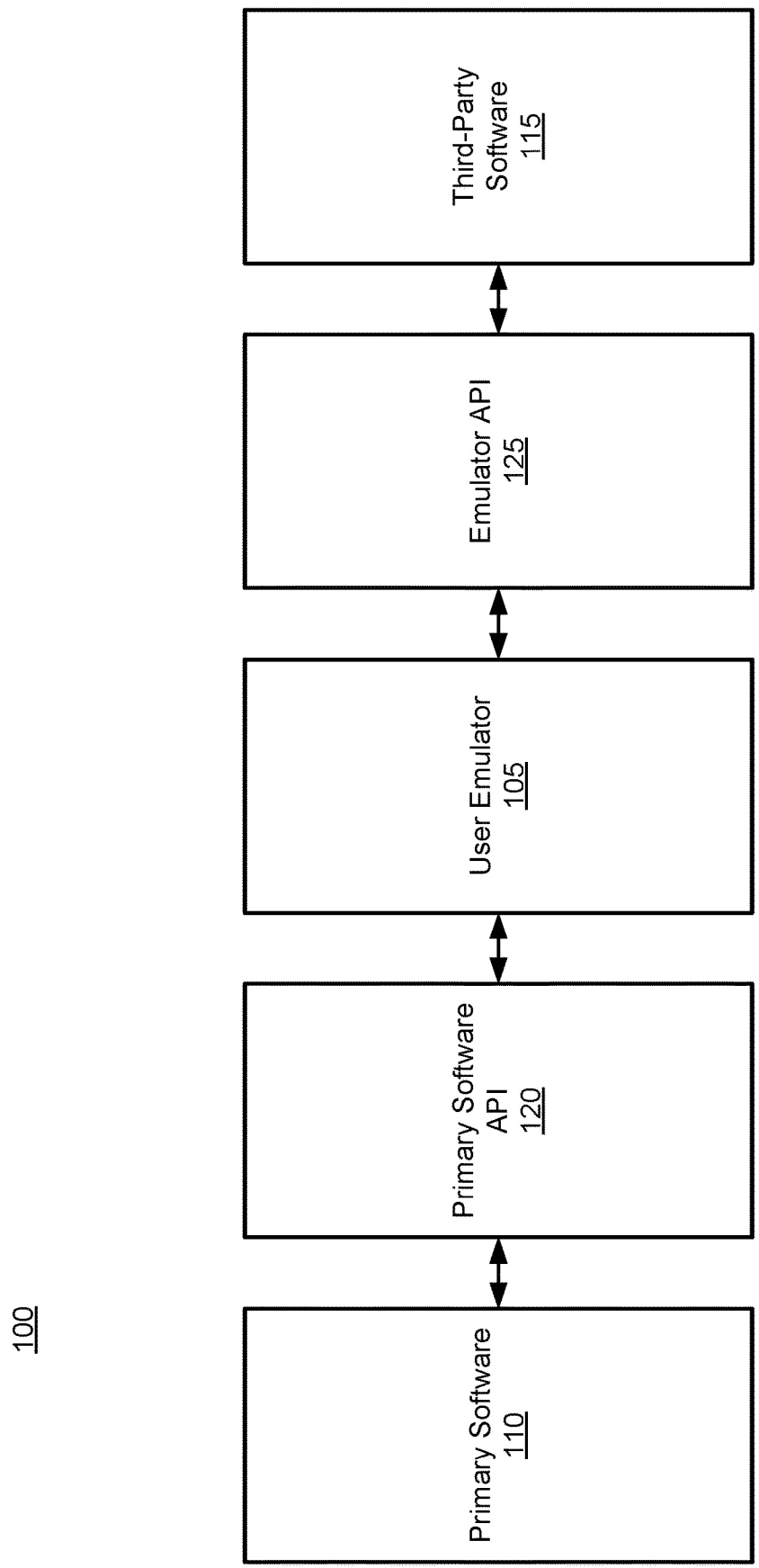
FIG. 1 is a conceptual diagram illustrating interfacing of a third-party application with a primary software platform through a user emulator, according to one embodiment.

The figures depict various embodiments of the present technology for purposes of illustration only.

DETAILED DESCRIPTION

Embodiments are described herein with reference to the accompanying drawings. Principles disclosed herein may, however, be embodied in many different forms and should not be construed as being limited to the embodiments set forth herein. In the description, details of well-known features and techniques may be omitted to avoid unnecessarily obscuring the features of the embodiments. In the drawings, like reference numerals in the drawings denote like elements.

Overview of Software Configurations

Embodiments relate to integration of a third-party software with a primary software or the integration of two or more different primary software platforms through one or more user emulators that emulate user input operations. The user emulator may enable interoperability between one or more primary software platforms and the third-party software by using the user emulator to communicate with the primary software platforms while using a call system (such as an application programming interface) to interface with the third-party software.

FIG. 1 is a conceptual diagram 100 illustrating a user emulator 105 for interfacing of a primary software 110 with a third-party software 115. A user emulator 105 can be used to replicate the physical user interaction through a graphical user interface or replicate triggering associated API calls. The user emulator 105 may automate the service at regular time intervals or upon request from another software module, obviating or reducing manual user operations. The user emulator 105 can emulate the user actions for reading and distributing data to third-party software and/or other primary software, or importing data from an outside source and write the data into the primary software. A user emulator 105 in a form of a plug-in to a web browser may be used. Alternatively, or additionally, a user emulator 105 in the form of any suitable code stack may be used to directly access the primary software 110.

In the diagram 100 shown, the user emulator 105 facilitates data exchange between the primary software 110 and the third-party software 115. The user emulator 105 may also be used to create a universal data repository that can be shared across disparate software platforms and/or to enable unified communication across disparate primary software platforms, discussed in detail below with reference to FIG. 2. An example of this would be sharing and processing patient medical data or patient scheduling data between two disparate medical software platforms or between a medical software platform and third-party software.

A primary software 110 (also referred to as "primary software platform" herein) described herein refers to software dedicated to a specific service or industry (e.g., medical service) operating with a specific data protocol. For example, the primary software 110 may be a healthcare software platform. Such primary software 110 may include, among others, electronic medical record (EMR) or medical practice management (PM) software platforms. These platforms generally do not share unified data structures and often involve the use of a specific data communication protocol (e.g., HL7) to interact and share data with each other and with third-party software 115. The primary software 110 may include locally hosted databases. Alternatively, or additionally, the primary software 110 may be web-based and include one or more private APIs.

A third-party software 115 (also referred to as "third-party application" and "third-party software platform" herein) described herein refers to a software application, such as a healthcare software platform, that can interoperate with the primary software 110 to enhance or enable the operation of the primary software 110. The third-party applications in the medical industry include, among others, applications for appointment scheduling, telemedicine, patient communication applications, staff communication applications, survey and rating applications, referral management systems, billing, document management and patient form management systems.

In some embodiments, the user emulator 105 may connect third-party software 115 to primary software 110 that utilizes a locally hosted database. In these embodiments, the user emulator 105 emulates physical user input operations to retrieve, export, and enter data. Examples of user input operations include, but are not limited to, mouse clicks, mouse movements, and the like. The user emulator 105 may also connect third-party software 115 to primary software 110 that is web-based and utilizes cloud-hosted database. In these embodiments, the user emulator 105 emulates user input operations by triggering the API calls of an API of the primary software, such as the primary software API 120, that would be triggered when user input operations are completed to retrieve, export, and enter data.

The user emulator 105 may store collected data on a cloud-based database associated with the user emulator 105. Alternatively, the user emulator 105 may store collected data on server of the user emulator 105. The user emulator 105 may also provide APIs, such as an emulator API 125, to the third-party software 115, allowing the third-party software 115 to interact with the primary software 110.

Figure 2:
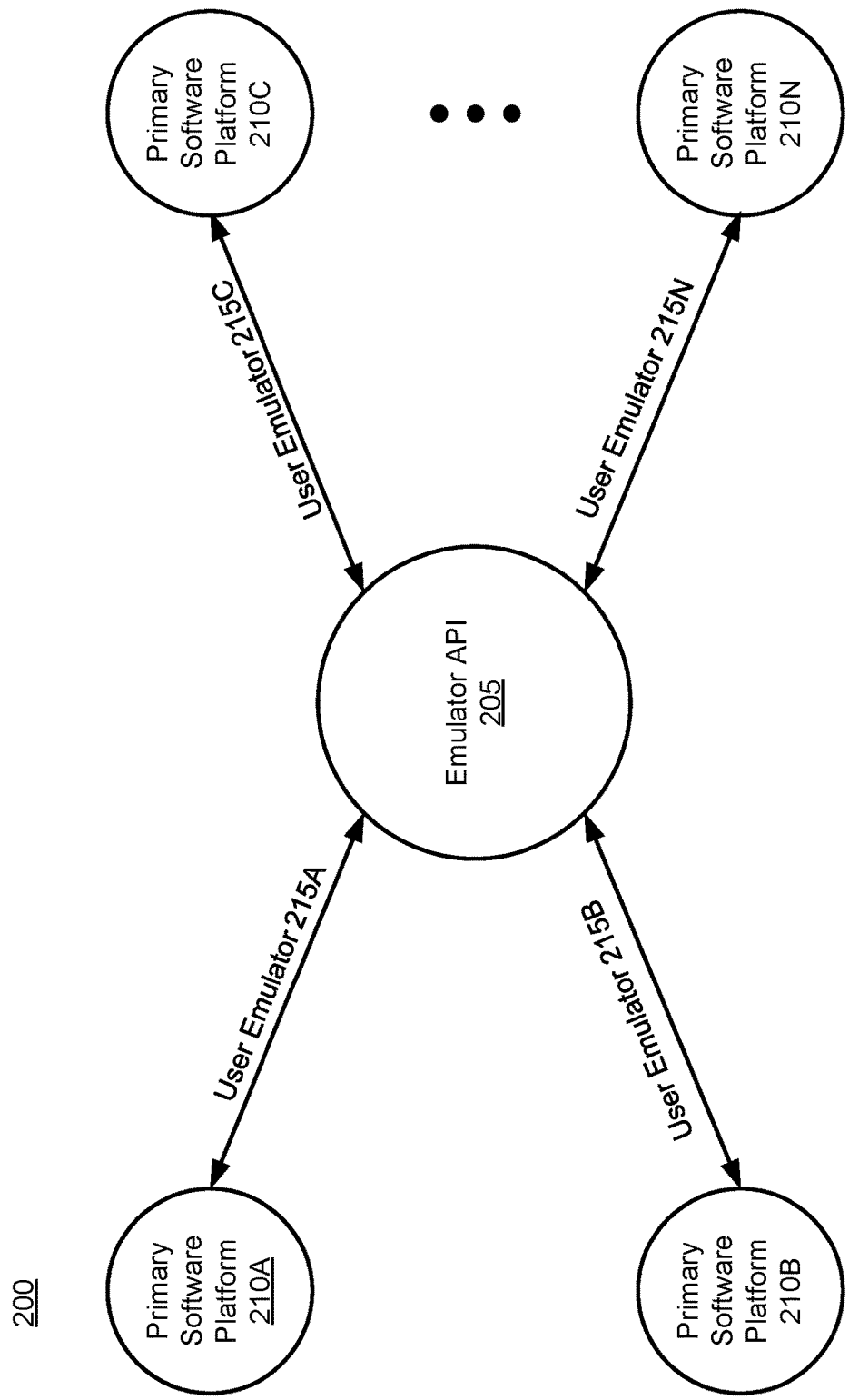
FIG. 2 is a conceptual diagram illustrating interfacing of multiple different primary software platforms utilizing multiple instances of user emulation, according to one embodiment.

FIG. 2 is a conceptual diagram 200 illustrating interfacing of multiple different primary software platforms utilizing multiple instances of user emulation. A user emulator can integrate multiple different primary software platforms, enabling data exchange between the platforms without requiring work on the part of either primary software platform. The user emulator can be used with each instance of primary software to retrieve, export, and enter data as well as retrieve data from a primary software platform and store that data on its own associated centralized cloud-based database. Emulator-owned centralized APIs, such as emulator API 205, are used to communicate and transact with a user emulator that is associated with each primary software. Multiple user emulators can be used with multiple primary software platforms to share data across a network of primary software platforms. For example, each primary software platform can interface with other primary software platforms through the emulator API and a respective user emulator. For example, primary software platform 210A may interface with other primary software platforms through user emulator 215A, primary software platform 210B may interface with other primary software platforms through user emulator 215B, primary software platform 210C may interface with other primary software platforms through user emulator 215C, and primary software platform 210N may interface with other primary software platforms through user emulator 215N. The multiple user emulators can collect data from primary software platforms, format and normalize the data, and re-distribute the data to other primary software platforms in a "Hub and Spokes" type model.

Example of User Emulator

Figure 3:
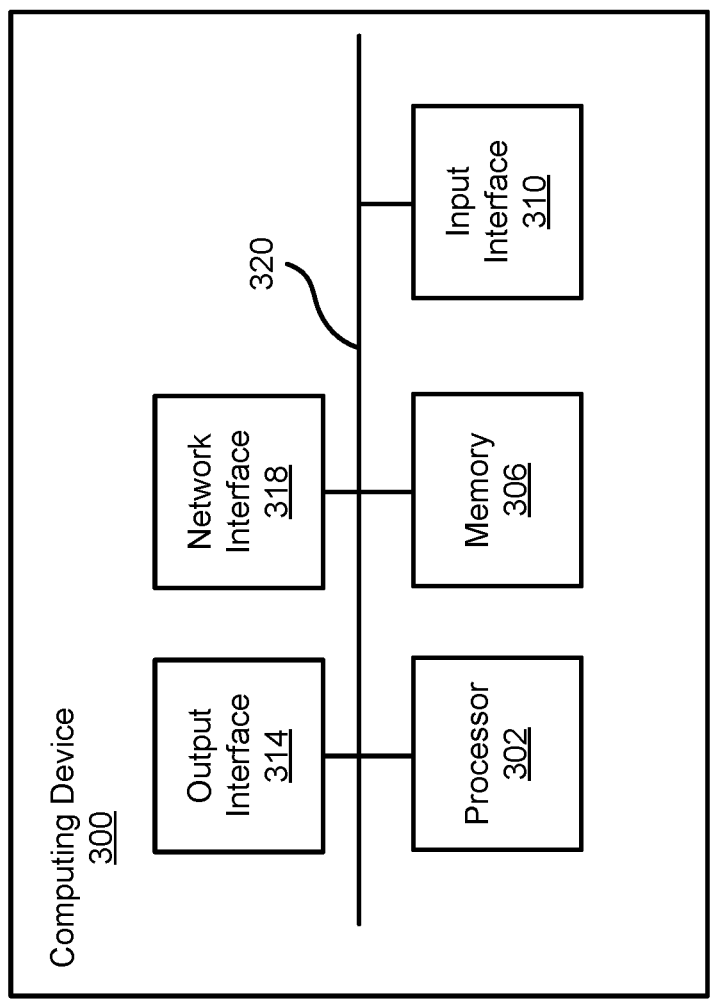
FIG. 3 is a block diagram illustrating a computing device for implementing a primary software and a user emulator, according to one embodiment.

FIG. 3 is a block diagram of a computing device 300 for implementing a primary software platform and a user emulator, according to one embodiment. The computing device 300 may include, among other components, a processor 302, a memory 306, an input interface 310, an output interface 314, a network interface 318 and a bus 320 connecting these components. The processor 302 retrieves and executes commands stored in memory 306. The memory 306 stores software components including, for example, operating systems, the primary software and the user emulator. The input interface 310 receives user interface devices such as a keyboard, a mouse and other peripheral devices. The output interface 314 is a component for providing the result of computation in various forms (e.g., image or audio signals). The network interface 318 enables the computing device 300 to communicate with other computing devices by a network.

In some embodiments, the primary software platform and the user emulator may be on the same computing device 300. In other embodiments, one or more of the user emulators and primary software platforms may be on separate computing devices or across multiple computing devices. In an alternative embodiment, the computing device 300 may store a third-party application in the memory 306 as an alternative to or in addition to the primary software platform. In this embodiment, the user emulator may be associated with the third-party application and enable the third-party application to access or perform operations on the data received from the primary software platform.

Figure 4A:
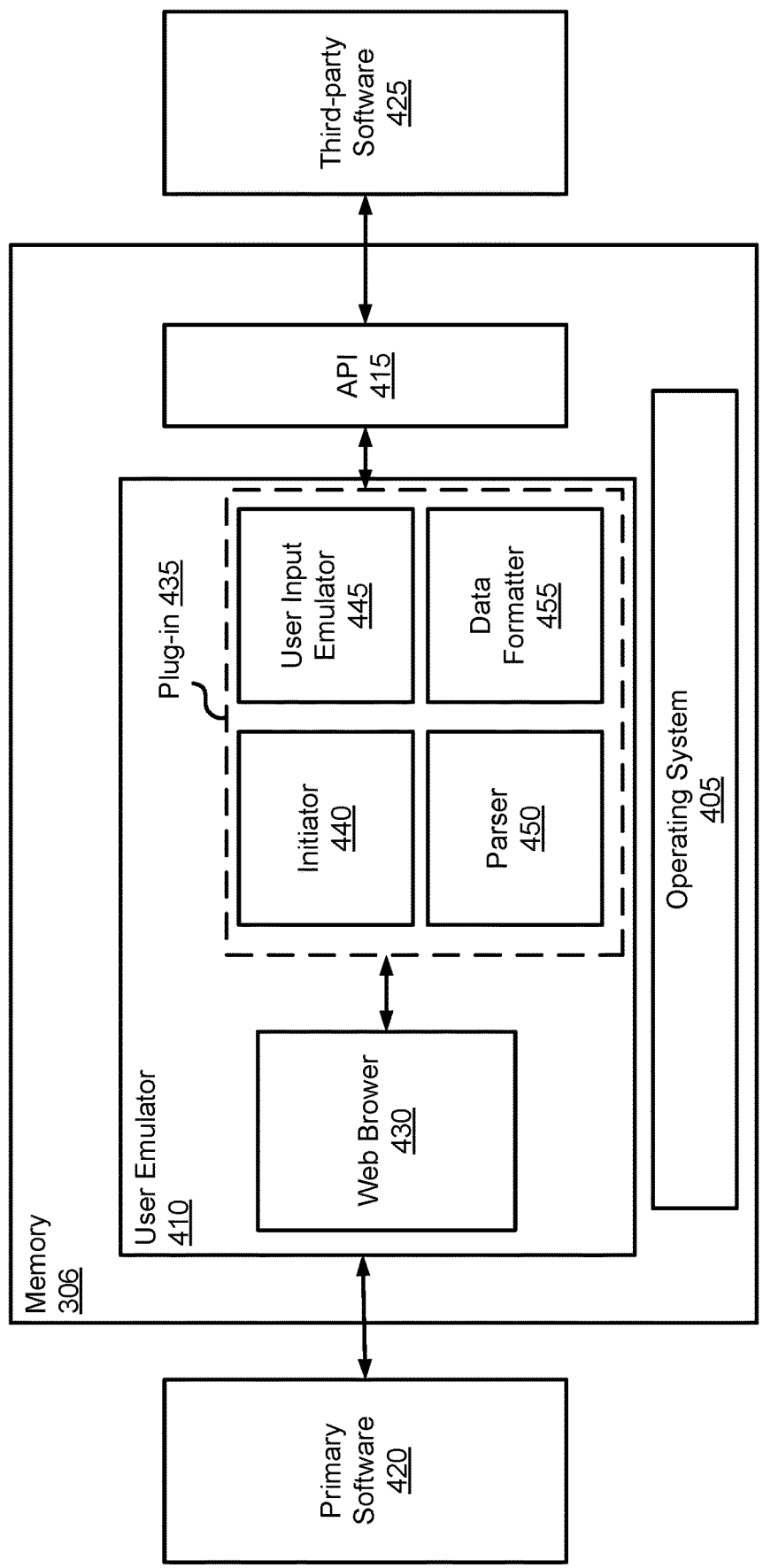
FIG. 4A is a block diagram illustrating software modules in the computing device of FIG. 3, according to one embodiment.

FIG. 4A is a block diagram illustrating software modules in the memory 306 of the computing device 300 of FIG. 3, according to one embodiment. The memory 306 stores, among other software modules, an operating system 405, a user emulator 410, and an API 415. The memory 306 may store other modules not illustrated in FIG. 4A. In the embodiment of FIG. 4A, the computing device 300 is illustrated as a separate device that enables interfacing between the primary software 420 and a third-party software 425. Although the user emulator 410, the API 415, the primary software 420 and the third-party software 425 are illustrated in FIG. 4A as being embodied on separate computing devices, two or more of these can be embodied on a single computing device. Alternatively, the functions of the user emulator 410, the API 415, the primary software 420, and the third-party software 425 may be distributed across multiple computing devices, for example, in cloud computing environment.

The operating system 405 is software that manages hardware and software resources on the computing device 300. The operating system 405 may be, for example, Unix, macOS, Linux, Microsoft Windows.

The user emulator 410 is a software module associated with the primary software 420 to enable interfacing with third-party software platforms, such as third-party software 425, or other primary software platforms. For different primary software platforms, a separate user emulator may be used as described below in detail with reference to FIG. 4B. The emulator 410 may include, among other components, a web browser 430 and a plug-in 435. The user emulator 410 emulates a user's input actions to perform various operations with the third-party software 425 or other primary software platforms, including but not limited to collecting data, reading data, writing data, and formatting the data.

The web browser 430 is a software application for accessing information using, for example, Internet protocol. The web browser 430 may be, for example, Google Chrome, Mozilla Firefox, Internet Explorer, Safari, Microsoft Edge, and Opera. The web browser 430 provides, among others, basic functionality for interfacing with the primary software 420 via a web interface.

The plug-in 435 expands the capability of the web browser 430 to integrate the operations of the primary software 420 and the third-party applications or other primary software platforms. The plug-in 435 may include, among other components, an initiator 440, a user input emulator 445, a parser 450 and a data formatter 455. The plug-in 435 may include other components not illustrated in FIG. 4A.

The initiator 440 enables emulation of authenticating a user on the primary software 420, the third-party software 425, and/or other primary software platforms (not illustrated). For this purpose, the initiator 440 may include combinations of user ID and password, store certificates for accessing these software applications and/or trigger calls to API 415. Moreover, the initiator 440 may perform other operations in conjunction with other modules such as determining the version and types of applications and establishing sessions based on such determination. The initiator 440 may also prompt the user to take manual operations to continue or establish the sessions.

The user input emulator 445 is a software module that emulates user's manual input operations (e.g., keyboard and mouse inputs) to access desired information from the primary software 420, the third-party software 425 or additional primary software platforms. That is, the user input emulator 445 may perform a series of automated tasks in conjunction with the parser 450 to retrieve desired information. The user input emulator 445 may also operate in conjunction with the data formatter 455 to write data into one or more of these software applications. In embodiments where the API 415 is available to interface with the third-party software 425, the user input emulator 445 may also trigger associated API calls via API 415 to perform the reading or writing operations associated with the third-party software 425. In embodiments where the API for the third-party software 425 is not available, the user input emulator 445 may interface directly with the third-party software 425, for example, via a web interface. Alternatively, or additionally, functions similar to those of the API 415 may be incorporated into the user emulator 410.

The parser 450 is a software module that parses information received from the primary software 420, third-party software 425, and/or other primary software platforms to perform various operations such as determining the version and the type of software applications. In one example, the parser 450 parses Cascading Style Sheets (CSS), Hypertext Markup Language (HTML) and/or JavaScript files to determine the types of application the user emulator 410 is interacting with, and provide information to other modules of the user emulator 410 to perform their operations. For example, the parser 450 may provide login screen information to the initiator 440 to log-in to a primary software, such as the primary software 420.

The data formatter 455 is a software module that converts data received from one software platform for further operations on another software platform. For example, the data formatter 455 may receive health medical data for multiple patients from a third-party software application, such as third-party software 425, via the parser 450 in one format via the API 415. The data formatter 455 may convert the received health medical data into a format compatible with the primary software 420, and provide the converted data to the primary software 420. Conversely, the data formatter 455 may read data from the primary software 420 in one format (e.g., CSS, HTML or JavaScript) and convert the read data into a format for sending to the third-party software 425 via the API 415.

Figure 4B:
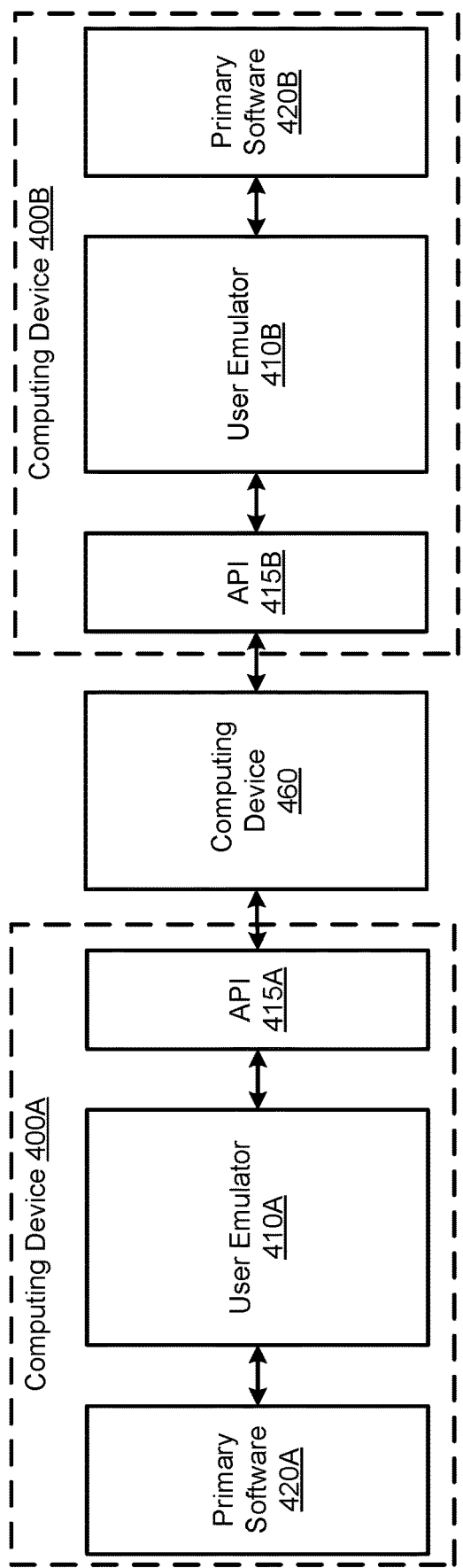
FIG. 4B is a block diagram illustrating interfacing between different primary software programs via user emulators, according to one embodiment.

FIG. 4B is a block diagram illustrating user emulators 410A, 410B for interfacing between different primary software platforms 420A, 420B, according to one embodiment. In the embodiment of FIG. 4B, each of the user emulators 410A, 410B is associated with a different primary software platform 420A, 420B, respectively. The communication between the two primary software platforms 420A, 420B are made through the user emulators 410A, 410B and APIs 415A, 415B, under the Hub and Spokes model as described above with reference to FIG. 3. Each of the APIs 415A, 415B communicate with a computing device 460 that functions as a Hub. The computing device 460 may perform, among other functions, formatting, storing and redistributing data that is shared between the primary software platforms 420A, 420B.

As described above, APIs for primary software platforms 420A, 420B may not be open or available, and hence, the user emulator 410A interfaces with the primary software 420A using a web interface that interfaces with one or more private APIs of the primary software 420A, while the user emulator 410B interfaces with the primary software 420B, also via a web interface that interfaces with one or more private APIs of the primary software 420B. The user emulators 410A, 410B may interface with each other via APIs 415A, 415B. In this way, the reading, writing or processing of data to or from the two distinct primary software programs 420A, 420B may be accomplished.

Although FIG. 4B illustrates the primary software 420A, the user emulator 410A, and its associated API 415A as being embodied on a single computing device 400A, and while the primary software 420B, the user emulator 410B and its associated API 415B as being embodied on another computing device 400B, various alternative arrangements on the distribution of these software applications and their software components are possible. For example, each of the primary software 420A, the user emulator 410A, and its associated API 415A may be embodied on separate computing devices or across multiple computing devices. Alternatively, the user emulators 410A, 410B and/or the APIs 415A, 415B can be embodied on a common computing device while the primary software programs 420A, 420B are embodied on separate computing devices. Further, more than two computing devices with different primary software platforms may be connected to the computing device 460. In addition, the system of FIG. 4B may be modified to include one or more third-party software platforms that interact with multiple primary software platforms via the user emulators and corresponding APIs.

Figure 5A:
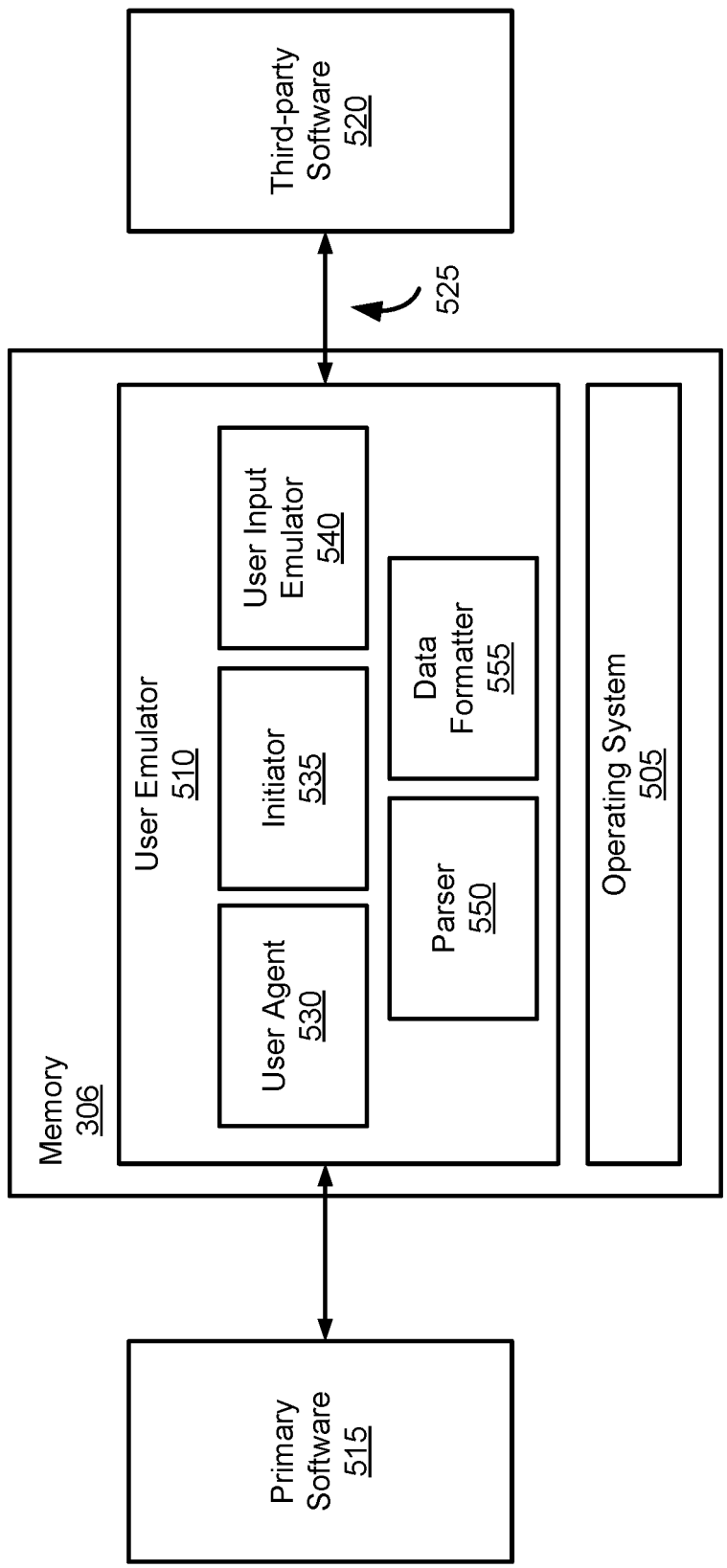
FIG. 5A is an alternative block diagram illustrating software modules in the computing device of FIG. 3, according to one embodiment.

FIG. 5A is an alternative block diagram illustrating software modules in the computing device 300 of FIG. 3, according to one embodiment. Similar to the block diagram illustrated in FIG. 4A, the alternative block diagram illustrated in FIG. 5A includes an operating system 505 and a user emulator 510 stored in the memory 306 of the computing device 300. The memory 306 may store other modules not illustrated in FIG. 5A. The operating system 505 may be similar or the same as the operating system 405 described in FIG. 4A.

In the embodiment of FIG. 5A, the computing device 300 is illustrated as a separate device that enables interfacing between the primary software 515 and a third-party software 520. Alternatively, the computing device 300, primary software 515, and third-party software 520 may be embodied on a single computing device, or may be distributed across multiple computing devices, for example, in a cloud computing environment.

In the block diagram shown in FIG. 5A, the user emulator 510 communicates with the third-party software 520 through a call system 525. The call system 525 may include an API, web socket, gPRC, or any other suitable communication method. Alternatively, or additionally, the functionality of the call system 525 may be integrated into the user emulator 510.

In the alternative block diagram shown, the user emulator 510 includes a user agent 530, an initiator 535, a user input emulator 540, a parser 550, and a data formatter 555. The emulator 510 emulates a user's input actions to perform various operations with the third-party software 520 or other primary software platforms, including but not limited to collecting data, reading data, writing data, and formatting the data.

The user agent 530 is any suitable software for accessing information. The user agent 530 provides, among others, basic functionality for interfacing with the primary software 515. For example, the user agent 530 may be a code stack that facilitates direct interaction between the user emulator 510 and the primary software 515. In some embodiments, the user agent 530 directly triggers API calls of an API of the primary software 515 by mimicking the functionality of a web browser.

The initiator 535 has the same or similar functionality to the initiator 440 described in detail with reference to FIG. 4A. For example, the initiator 535 enables emulation of authenticating a user on the primary software 515, the third-party software 520, and/or other primary software platforms. The initiator 535 may include combinations of user ID and password, store certificates for accessing these software applications and/or trigger calls to the call system 525. In addition, the initiator 535 may perform operations in conjunction with other modules such as determining the version and types of applications and establishing sessions based on such determination. Further, the initiator 535 may prompt the user to take manual operations to continue or establish the sessions.

The user input emulator 540 has the same or similar functionality to the user input emulator 445 described with reference to FIG. 4A. For example, the user input emulator 540 emulates user input operations to access desired information from the primary software 515, the third-party software 520, and/or other primary software platforms. The user input emulator 540 may also operate in conjunction with the parser 550 to retrieve desired information, operate in conjunction with the formatter 555 to write data into one or more software applications, and the like. In embodiments where the call system 525 is available to interface with the third-party software 520, the user input emulator 540 may also trigger associated calls via the call system 525 to perform the reading or writing operations associated with the third-party software 520. In other embodiments where a call system for the third-party software 520 is not available, the user input emulator 540 may interface directly with the third-party software 520, for example, via a web interface. The emulator 540 may also provide login screen information to the initiator 535 to log-in to a primary software 515.

The parser 550 has the same or similar functionality to the parser 450 described with reference to FIG. 4A. For example, the parser 550 is a software module that parses information received from the primary software 515, third-party applications, and/or other primary software platforms to perform various operations such as determining the version and the type of software applications.

The data formatter 555 has the same or similar functionality to the data formatter 455 described with reference to FIG. 4A. For example, the data formatter 555 is a software module that converts data received from one software application for further operations on another software application. The data formatter 555 may convert the pages of information from the third-party software 520 into a format compatible with the primary software 515, and provide the converted page of information to the to the primary software 515. Conversely, the data formatter 555 may read a page of information from the primary software 515 in one format (e.g., CSS, HTML or JavaScript) and convert the read page of information into a format for sending to the third-party software 520.

The user emulator 510, primary software 515, and/or third-party software 520 may be embodied on separate computing devices, as shown in the alternative block diagram illustrated in FIG. 5A. Alternatively, or additionally, two or more of these can be embodied on a single computing device. Further, the functions of the user emulator 510, call system 525, primary software 515, and/or third-party software 520 may be distributed across multiple computing devices, for example, in a cloud computing environment.

Figure 5B:
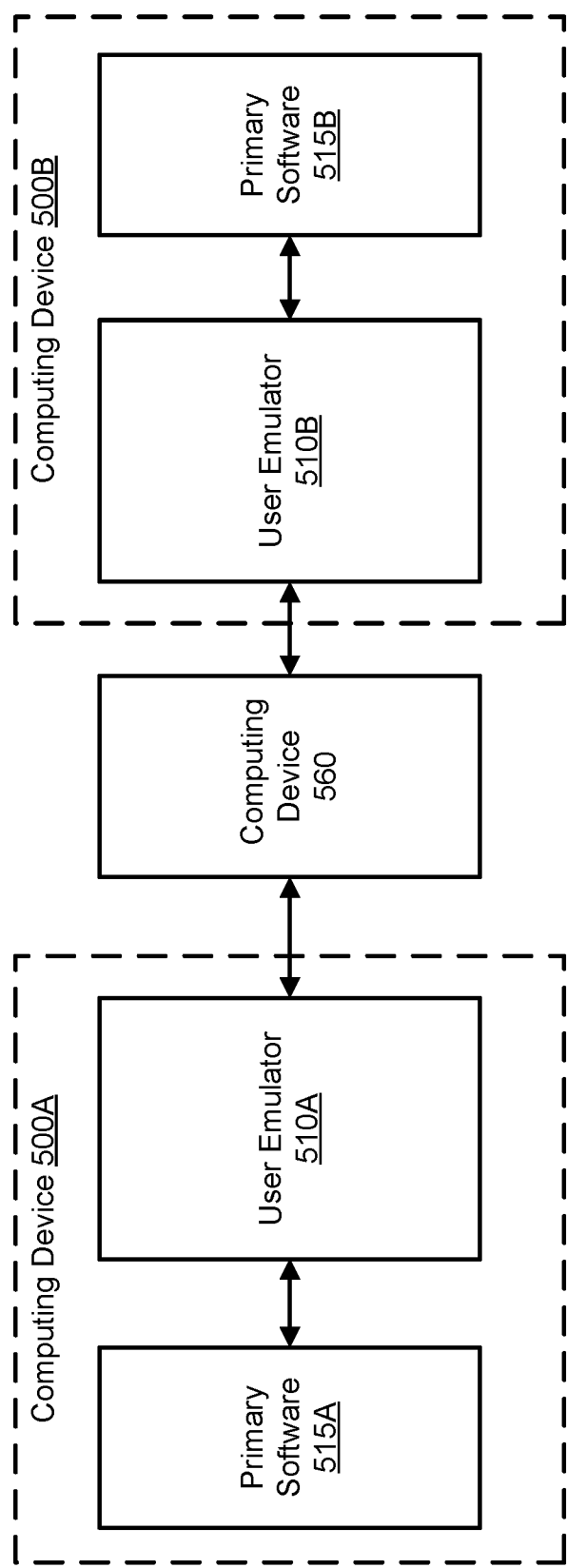
FIG. 5B is an alternative block diagram illustrating interfacing between different primary software programs via user emulators, according to one embodiment.

FIG. 5B is an alternative block diagram illustrating user emulators 510A, 510B for interfacing between different primary software platforms 515A, 515B, according to one embodiment. In the embodiment of FIG. 5B, each of the user emulators 510A, 510B is associated with a different primary software platforms 515A, 515B, respectively. The communication between the two primary software platforms 515A, 515B are made through the user emulators 510A, 510B, under the Hub and Spokes model as described above with reference to FIG. 3. Each of the user emulators 510A, 510B communicate with a computing device 560 that functions as a Hub through any suitable communication method. Similar to the computing device 460 described with reference to FIG. 4B, the computing device 560 may perform, among other functions, formatting, storing and redistributing data that is shared between the primary software platforms 515A, 515B. In this way, the reading, writing or processing of data to or from the two distinct primary software platforms 515A, 515B may be accomplished.

Although FIG. 5B illustrates the primary software 515A and the user emulator 510A as being embodied on a single computing device 500A, and while the primary software 515B and the user emulator 510B as being embodied on another computing device 500B, various alternative arrangements on the distribution of these software applications and their software components are possible. For example, each of the primary software 515A and the user emulator 510A may be embodied on separate computing devices or across multiple computing devices. Alternatively, the user emulators 510A, 510B may be embodied on a common computing device while the primary software 515A, 515B are embodied on separate computing devices. Further, more than two computing devices with different primary software platforms may be connected to the computing device 560. In some embodiments, the system of FIG. 5B may be modified to include one or more third-party software platforms that interact with multiple primary software platforms via the user emulators.

FIG. 6 is a flow chart of a method 600 for interfacing healthcare software platforms, according to one embodiment. In the method 600 shown, a first healthcare software platform and a second healthcare software platform are accessed 605. The first healthcare software platform may be a primary software (e.g., primary software 420, primary software 515) and/or a third-party software (e.g., third-party software 425, third-party software 520). Similarly, the second healthcare software platform may be a primary software (e.g., primary software 420, primary software 515) and/or a third-party software (e.g., third-party software 425, third-party software 520). The first healthcare software platform and/or second healthcare software platform may be accessed through an API of a user emulator, an API of the first healthcare software platform, an API of the second healthcare software platform, and the like. First sessions are initiated 610 with the first healthcare software platform and the second healthcare software platform. First sessions may be initiated by performing authentication of a user by sending authentication information of the user to the first healthcare software platform and the second healthcare platform.

First user input operations are emulated 615 on the first healthcare software platform to receive a first page of information. In some embodiments, first user input operations are emulated by triggering one or more API calls of the first healthcare software platform. The first page of information may be parsed to determine a version and a type of the first healthcare software platform. A first format of the first page of information is converted 620 to a second format to write the converted first page of information to the second healthcare software platform. For example, the first healthcare software platform may be a primary software platform, and the second healthcare software platform may be a third-party software platform. Using this method 600, the first page of information may be provided to the third-party software platform in a format that is compatible with the third-party software platform.

Figure 7:
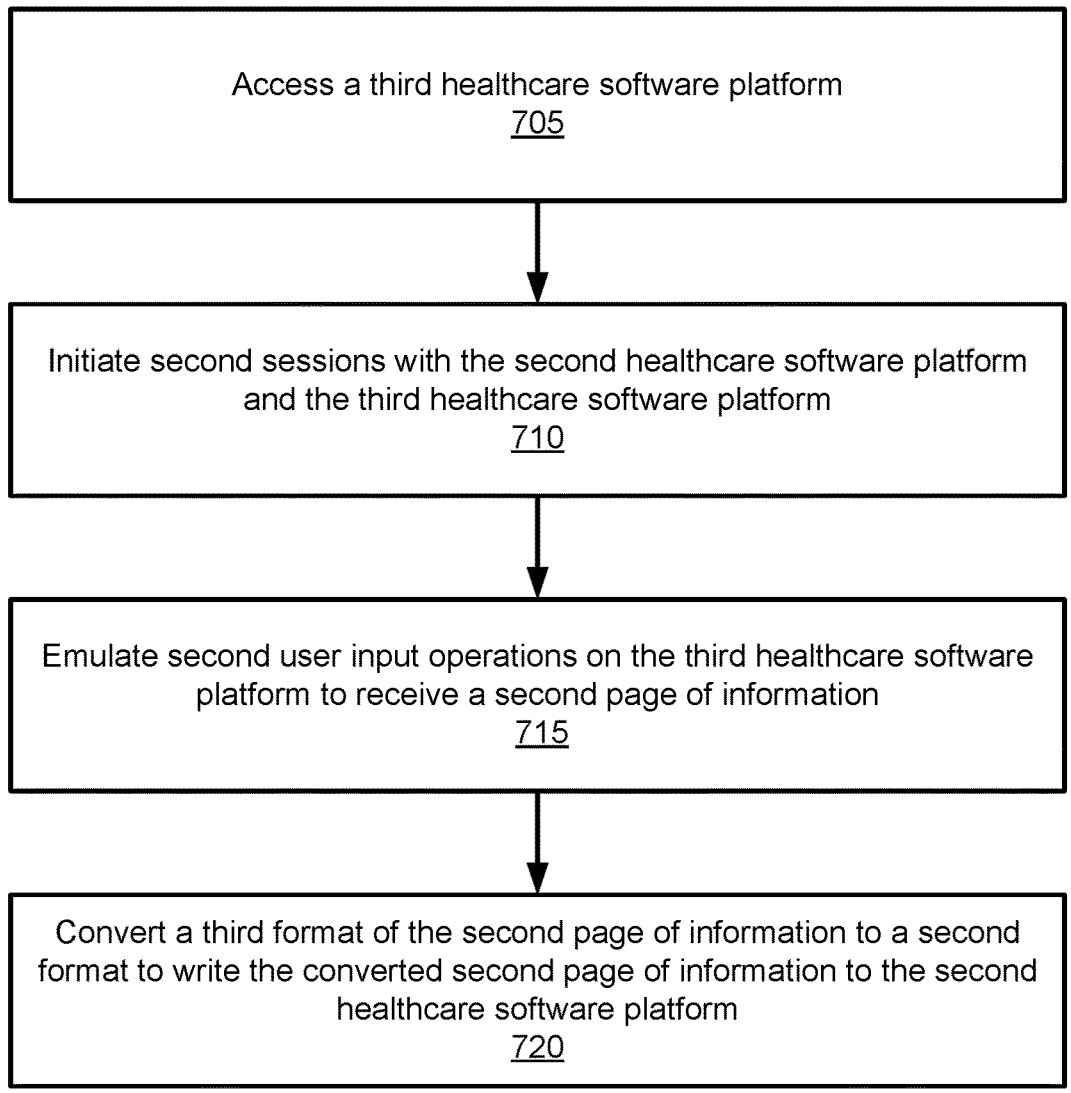
FIG. 7 is a flow chart of an additional method for interfacing healthcare software platforms, according to one embodiment.

FIG. 7 is a flow chart of an additional method 700 for interfacing healthcare software platforms, according to one embodiment. Through this method, a hub and spoke model is embodied where the user emulator functions as the hub and the healthcare software platforms function as spokes. In the method 700 shown, a third healthcare software platform is accessed 705. The third healthcare software platform may be a primary software (e.g., primary software 420, primary software 515) and/or a third-party software (e.g., third-party software 425, third-party software 520). Second sessions are initiated 710 with the second healthcare software platform and the third healthcare software platform. Second user input operations are emulated 715 on the third healthcare software platform to receive a second page of information. In some embodiments, the first user input operations are emulated by triggering API calls of a first API, and the second user input operations are emulated by triggering API calls of a second API distinct from the first API. For example, the first API may be an API of the first healthcare software platform, and the second API may be an API of the third healthcare software platform. A third format of the second page of information is converted 720 to a second format to write the converted second page of information to the second healthcare software platform. For example, the third healthcare software platform may be a primary software platform, and the second healthcare software platform may be a third-party software platform. Using this method 700, a second page of information may be provided to the third-party software platform in a format that is compatible with the third-party software platform.

The foregoing description of the embodiments has been presented for the purposes of illustration. It is not intended to be exhaustive or to limit the patent rights to the precise forms disclosed. Persons skilled in the relevant art can appreciate that many modifications and variations are possible in light of the above disclosure.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may include a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may include information resulting from a computing process, where the information is stored on a non-transitory, tangible computer readable medium and may include any embodiment of a computer program product or other data combination described herein.

Finally, the language used in the specification has been principally selected for readability and instructional purposes, and it may not have been selected to delineate or circumscribe patent rights. It is therefore intended that the scope of the patent rights be limited not by this detailed description, but rather by any claims at issue on an application based hereon. Accordingly, the disclosure of the embodiments is intended to be illustrative, but not limiting, of the scope of the patent rights, which is set forth in the following claims.

What is claimed is:

1. A computing device, comprising:
    a processor; and
    memory storing instructions thereon, the instructions when executed by the processor cause the processor to:
        access a first healthcare software platform and a second healthcare software platform disparate from the first healthcare software platform,
        initiate first sessions with the first healthcare software platform and the second healthcare software platform,
        emulate first user input operations on the first healthcare software platform without invoking a public application programming interface (API) call to the first healthcare software platform,
        responsive to the emulation of the first user input operations, obtain a first page of information in a first format, and
        convert the first format of the first page of information to a second format to write the converted first page of information to the second healthcare software platform.

2. The computing device of claim 1, wherein the first sessions are initiated by performing authentication of a user by sending authentication information of the user to the first healthcare software platform and the second healthcare software platform.

3. The computing device of claim 1, wherein the memory further comprises instructions that cause the processor to parse the first page of information to determine a version and a type of the first healthcare software platform before converting the format of the first page information.

4. The computing device of claim 1, wherein the memory stores an application programming interface (API) that is executed by the processor to communicate with the second healthcare software platform.

5. The computing device of claim 1, wherein the memory further stores instructions, when executed by the processor cause the processor to:
    access a third healthcare software platform disparate from the first healthcare software platform and the second healthcare software platform,
    initiate second sessions with the second healthcare software platform and the third healthcare software platform,
    emulate second user input operations on the third healthcare software platform to receive a second page of information, and
    convert a third format of the second page of information to the second format to write the converted second page of information to the second healthcare software platform.

6. The computing device of claim 1, wherein the second user input operations are emulated by triggering one or more API calls of a second API distinct from the first API.

7. The computing device of claim 1, wherein the first healthcare software platform is a primary software platform, and wherein the second healthcare software platform is a third-party software.

8. The computing device of claim 1, wherein the first user input operations emulate mouse clicks or mouse movements on the first healthcare software platform.

9. The computing device of claim 1, wherein the first page information includes information in at least one of a HTML, CSS, or JavaScript format.

10. A method comprising:
    accessing a first healthcare software platform and a second healthcare software platform disparate from the first healthcare software platform;
    initiating first sessions with the first healthcare software platform and the second healthcare software platform;
    emulating first user input operations on the first healthcare software platform without invoking a public application programming interface (API) call to the first healthcare software platform;
    responsive to the emulation of the first user input operations, obtaining a first page of information in a first format; and
    converting the first format of the first page of information to a second format to write the converted first page of information to the second healthcare software platform.

11. The method of claim 10, wherein the sessions are initiated by performing authentication of a user by sending authentication information of the user to the first healthcare software platform and the second healthcare software platform.

12. The method of claim 10, further comprising:
parsing the first page of information to determine a version and a type of the first healthcare software platform before converting the format of the first page of information.

13. The method of claim 10, wherein the second healthcare software platform is accessed through an application programming interface (API).

14. The method of claim 10, further comprising:
accessing a third healthcare software platform disparate from the first healthcare software platform and the second healthcare software platform;
initiating second sessions with the second healthcare software platform and the third healthcare software platform;
emulating second user input operations on the third healthcare software platform to receive a second page of information; and
converting a third format of the second page of information to the second format to write the converted second page of information to the second healthcare software platform.

15. The method of claim 10, wherein the second user input operations are emulated by triggering one or more API calls of a second API distinct from the first API.

16. The method of claim 10, wherein the first user input operations emulate mouse clicks or mouse movements on the first healthcare software platform.

17. The method of claim 10, wherein the first page information includes information in at least one of a HTML, CSS, or JavaScript format.

18. A non-transitory computer-readable medium storing instructions that when executed by one or more processors cause the one or more processors to:
access a first healthcare software platform and a second healthcare platform disparate from the first healthcare software platform;
initiate first sessions with the first healthcare software platform and the second healthcare software platform;
emulate first user input operations on the first healthcare software platform without invoking a public application programming interface (API) call to the first healthcare software platform;
responsive to the emulation of the first user input operations, obtain a first page of information in a first format; and
convert a first format of the first page of information to a second format to write the converted first page of information to the second healthcare software platform.

19. The non-transitory computer-readable medium of claim 18, wherein the first sessions are initiated by performing authentication of a user by sending authentication information of the user to the first healthcare software platform and the second healthcare software platform.

20. The non-transitory computer-readable medium of claim 18, wherein the instructions further cause the one or more processors to parse the first page of information to determine a version and a type of the first healthcare software platform before converting the format of the first page of information.

* * * * *